United States Patent
Wilcox et al.

(10) Patent No.: US 8,163,971 B2
(45) Date of Patent: Apr. 24, 2012

(54) METHOD OF PROVIDING HEAT FOR CHEMICAL CONVERSION AND A PROCESS AND SYSTEM EMPLOYING THE METHOD FOR THE PRODUCTION OF OLEFIN

(75) Inventors: Richard J. Wilcox, West Caldwell, NJ (US); Sanjeev Ram, Berkeley Heights, NJ (US); Ajay Gami, East Brunswick, NJ (US); Robert Brummer, Wharton, NJ (US); Joseph Romeo, West Paterson, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 516 days.

(21) Appl. No.: 12/381,800

(22) Filed: Mar. 17, 2009

(65) Prior Publication Data
US 2010/0240940 A1 Sep. 23, 2010

(51) Int. Cl.
*C07C 5/32* (2006.01)
(52) U.S. Cl. .................. 585/910; 585/911; 585/440
(58) Field of Classification Search .............. 585/911, 585/910, 440
See application file for complete search history.

(56) References Cited

U.S. PATENT DOCUMENTS

| | | | |
|---|---|---|---|
| 4,628,136 | A | 12/1986 | Sardina |
| 4,769,506 | A | 9/1988 | Kosters |
| 4,774,378 | A | 9/1988 | Faure et al. |
| 4,778,941 | A | 10/1988 | Tagamolila |
| 5,043,500 | A | 8/1991 | Tagamolila |
| 5,376,613 | A | 12/1994 | Dellinger et al. |
| 5,510,552 | A | 4/1996 | Dellinger et al. |
| 5,658,452 | A | 8/1997 | Heyse et al. |
| 6,100,436 | A | 8/2000 | Wiede, Jr. et al. |

FOREIGN PATENT DOCUMENTS
KR 10-2007-0012898 A 1/2007

OTHER PUBLICATIONS

International Search Report and Written Opinion issued Oct. 11, 2010 in corresponding International Application No. PCT/US2010/026910 (8 pages).
"Thermocompressors", Fox Valve Development Corp., http://www.foxvalve.com/thermocompressors/index.html (2001).

*Primary Examiner* — Thuan Dinh Dang
(74) *Attorney, Agent, or Firm* — Osha • Liang LLP

(57) ABSTRACT

A method and system for providing heat to a chemical conversion process is advantageously employed in the production of olefin by the catalytic dehydrogenation of a corresponding hydrocarbon. The catalytic dehydrogenation process employs diluent steam operating at a steam to oil ratio which can be 1.0 or below and relatively low steam superheater furnace temperature. The process and system are advantageously employed for the production of styrene by the catalytic dehydrogenation of ethylbenzene.

10 Claims, 4 Drawing Sheets

… (US 8,163,971 B2)

METHOD OF PROVIDING HEAT FOR CHEMICAL CONVERSION AND A PROCESS AND SYSTEM EMPLOYING THE METHOD FOR THE PRODUCTION OF OLEFIN

BACKGROUND

1. Field of the Invention

The invention herein relates to a method for supplying sensible heat to a chemical conversion process, and particularly to a process and system for the production of an olefin, more particularly to a process and system for the production of styrene by means of the dehydrogenation of ethylbenzene.

2. Description of the Related Art

The production of styrene by the catalytic dehydrogenation of ethylbenzene is well known in the art. Typically, a feed containing steam and ethylbenzene is contacted with a catalyst in a reactor at an inlet temperature of from about 600° C. to about 650° C. to effect conversion. Steam is heated to a predetermined temperature in a steam superheater. The steam supplies at least some of the heat needed for the reaction and, as a diluent, reduces the partial pressure of the styrene and hydrogen, thereby shifting the reaction equilibrium towards the production of styrene.

U.S. Pat. No. 4,628,136 to Sardina discloses a dehydrogenation process for the production of styrene from ethylbenzene in the presence of steam. Ethylbenzene and water form an azeotropic mixture which boils at a lower temperature than either ethylbenzene or water. Most of the ethylbenzene/water feed is vaporized by condensing overhead vapor from the ethylbenzene/styrene splitter system. This feature saves energy since less steam needs to be used to vaporize the feed stream and less cooling water is required to condense the overhead vapor of the ethylbenzene/styrene splitter The mass steam to oil ratio, i.e., the ratio of steam to ethylbenzene contained in a feedstream ("oil") on a weight basis, is an important factor in the dehydrogenation of ethylbenzene. In the past, styrene production plants operated at overall steam/oil weight ratios of 1.3 to 1.7. Improved catalysts have allowed the process to operate at steam/oil weight ratios of about 1.0 with acceptable reductions in yield or ethylbenzene conversion.

To supply the proper amount of heat to the system at an overall steam/oil weight ratio of 1.0 or lower, the temperature at the outlet of the steam superheater would have to be increased to 950° C. or even higher. However, superheater temperatures above 927° C. require the use of special and costly metallurgy. It would be advantageous to have a system which operates at both low steam/oil ratios and lower temperatures.

SUMMARY

In an embodiment of the present invention a method is provided herein for providing heat to a chemical conversion process stream containing at least one chemical reactant. The method includes the steps of (a) superheating a heat transfer fluid; (b) transferring heat from the superheated heat transfer fluid to the process stream; (c) dividing at least some of the heat transfer fluid into a first portion and a second portion; (d) pressurizing the first portion of heat transfer fluid; (e) recycling the pressurized first portion of heat transfer fluid to superheating step (a); and, (f) introducing the second portion of the heat transfer fluid into the process stream.

In another embodiment a process is provided herein for the production of an olefin by the catalytic dehydrogenation of a feedstream which contains a hydrocarbon having at least a portion of the molecule capable of undergoing dehydrogenation such as, for example, alkyl compounds (e.g., ethane, propane, butane, etc.) and alkylaromatic compounds (e.g., ethylbenzene, n-propylbenzene, cermene, etc). The process comprises transferring heat from superheated steam, which may already have been heated by indirect heat exchange, to a process stream containing diluent steam and the hydrocarbon capable of being dehydrogenated, the additional heat from the superheated steam being sufficient to effect catalytic dehydrogenation of at least a portion of the hydrocarbon capable of being dehydrogenated in a reaction zone, wherein after transferring the heat the superheated steam becomes spent steam. The spent steam is split into two streams: a recycle steam and a process steam. The recycle steam is pressurized through the use of a thermocompressor. It is then combined with motive steam and heated to a predetermined temperature in the steam superheater. The process steam is reheated to generate superheated steam and is combined with the feedstream which contains the hydrocarbon capable of being dehydrogenated before entering the dehydrogeneration reactor. The net result is more superheated steam available for heat transfer compared to the steam required to satisfy the steam/oil ratio in the reactor.

Also provided is a system for the production of styrene by the catalytic dehydrogenation of ethylbenzene.

The process and system described herein advantageously can be operated at a steam/oil ratio of 1.0 or below while requiring a superheated steam temperature low enough to avoid the need for specialized metallurgy for the steam superheater furnace and transfer lines (i.e., the piping connections for transferring superheated steam from the steam superheater furnace to the heat exchangers and reactors and back to the steam superheater). This scheme could also be used at higher mass steam/oil ratios.

BRIEF DESCRIPTION OF THE DRAWINGS

Various embodiments are described below with reference to the drawings wherein.

DETAILED DESCRIPTION OF PREFERRED EMBODIMENT(S)

Figure 1:
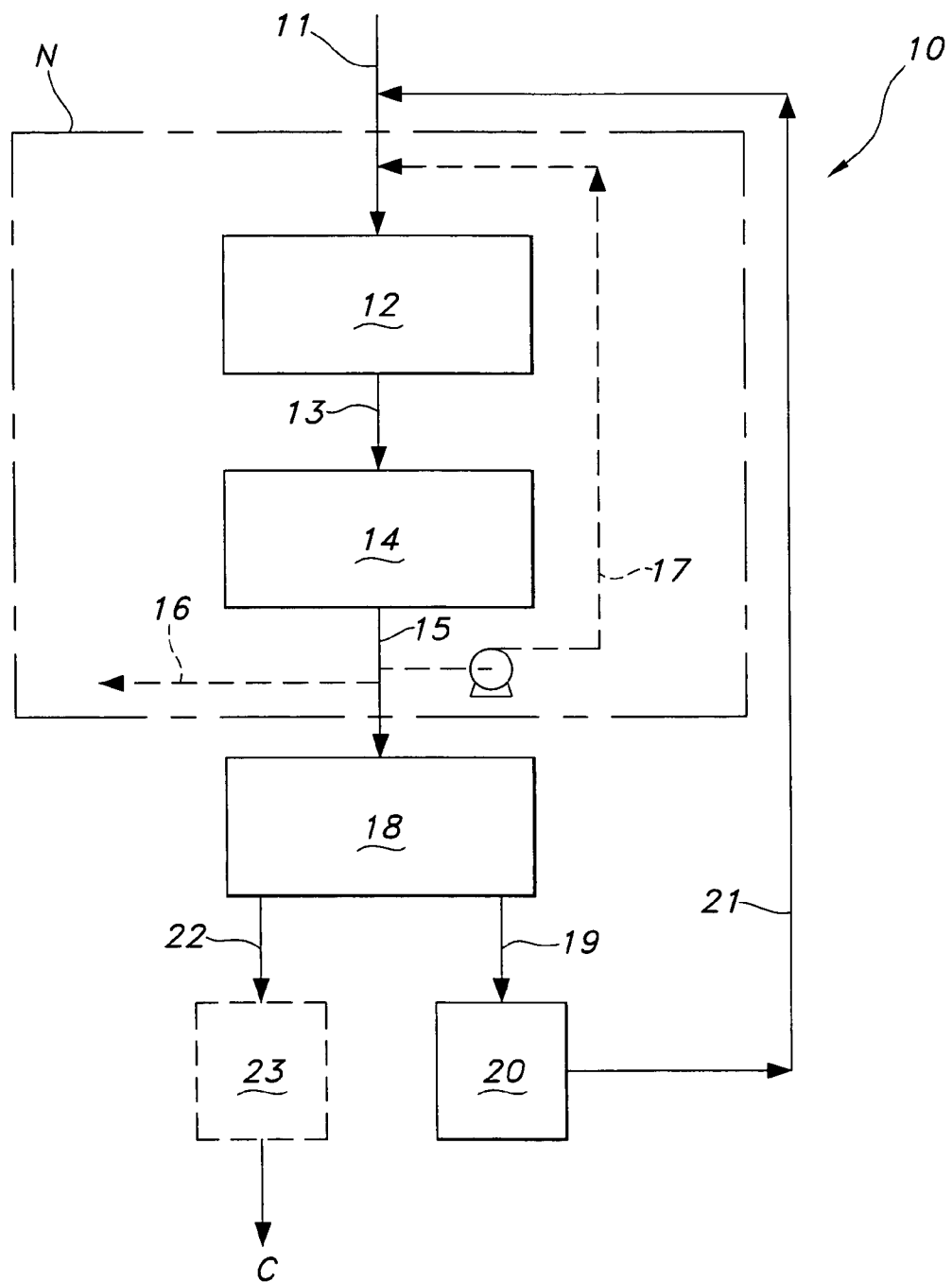
FIG. 1 is a schematic flow diagram of a method for supplying sensible heat to a process stream of a chemical conversion process.

Referring to FIG. 1, a method for providing sensible heat to a process stream of a chemical conversion process is illustrated. The method employs a heat transfer fluid. The preferred heat transfer fluid for the chemical conversion process described herein is steam.

Heat transfer fluid stream 11 is superheated in a superheating step 12 to produce a superheated heat transfer fluid 13. Heat is then transferred in a heat transfer step 14 from the superheated heat transfer fluid to the process stream of a chemical conversion process which contains one or more reactant chemicals. The effluent from the heat transfer step 14 is a spent heat transfer fluid stream 15.

Optionally, a portion 16 of the spent heat transfer fluid stream 15 may be drawn off and sent to other processes. Also optionally, a portion 17 of the spent heat transfer fluid stream 15 may be drawn off and recycled to the superheating step 12 via a conventional pressure increasing step (not pictured). The method 10 as outlined in FIG. 1 includes one outlined section N including superheating step 12 and heat transfer step 14. However, in other embodiments, the method of the present invention can include more that one outlined sections N incorporated in any manner known in the art. In short, method 10 can include multiple superheating steps 12 and heat transfer steps 14. The steps 12 and 14 may be repeated in the same or different units of equipment. Alternatively, method 10 can be performed without outlined section N.

At least a portion of the spent heat transfer fluid stream 15 is divided in a dividing step 18 into a first portion 19 and a second portion 22. The first portion 19 is sent to a step 20 in which the heat transfer fluid stream is pressurized. The pressurizing step can be performed by a mechanical compressor or any other means known in the art. A preferred compressor is a thermocompressor which uses a compression fluid. For example, a high pressure compression steam is introduced into the thermocompressor to pressurize first portion 19 of spent heat transfer steam 15 which is at a relatively lower pressure. The compressed steam 21 (including the steam introduced as spent steam and the steam introduced as compression steam) is then recycled and reheated in superheating step 12. The amount of compression steam is adjusted to make up for steam drawn off from the system.

The second portion 22 of spent heat transfer fluid 15 is introduced into the process stream C of the chemical conversion process. Optionally, the second portion 22 of the heat transfer fluid can be reheated in second superheating step 23. The method described herein is advantageously employed in a dehydrogenation process as described below.

The present dehydrogenation process relates to the production of an olefinic hydrocarbon by means of the dehydrogenation of a corresponding hydrocarbon. Steam is used as a diluent and provides the source of part of the heat for the dehydrogenation reaction, which is endothermic. Preferably, two reactors are used. The reactors can alternatively be axial flow or radial flow or parallel flow reactors. Such reactors are known in the art.

While the process and system herein can be used for any dehydrogenation process employing steam as a diluent and heat transfer medium, the technology described herein is particularly advantageous for the production of styrene from ethylbenzene and is illustrated herein for styrene production. Other processes in which the present invention can be employed include the production of vinyl toluene from ethyl toluene, the dehydrogenation of propane to propylene, and the dehydrogenation of butane to $C_4$ compounds such as 1-butene, 2-butene, or butadiene.

It is understood that certain equipment such as valves, piping, indicators and controls, and the like have been omitted from the drawings to facilitate the description thereof, and that the appropriate placement of such equipment is deemed to be within the scope of one skilled in the art.

Figure 2:
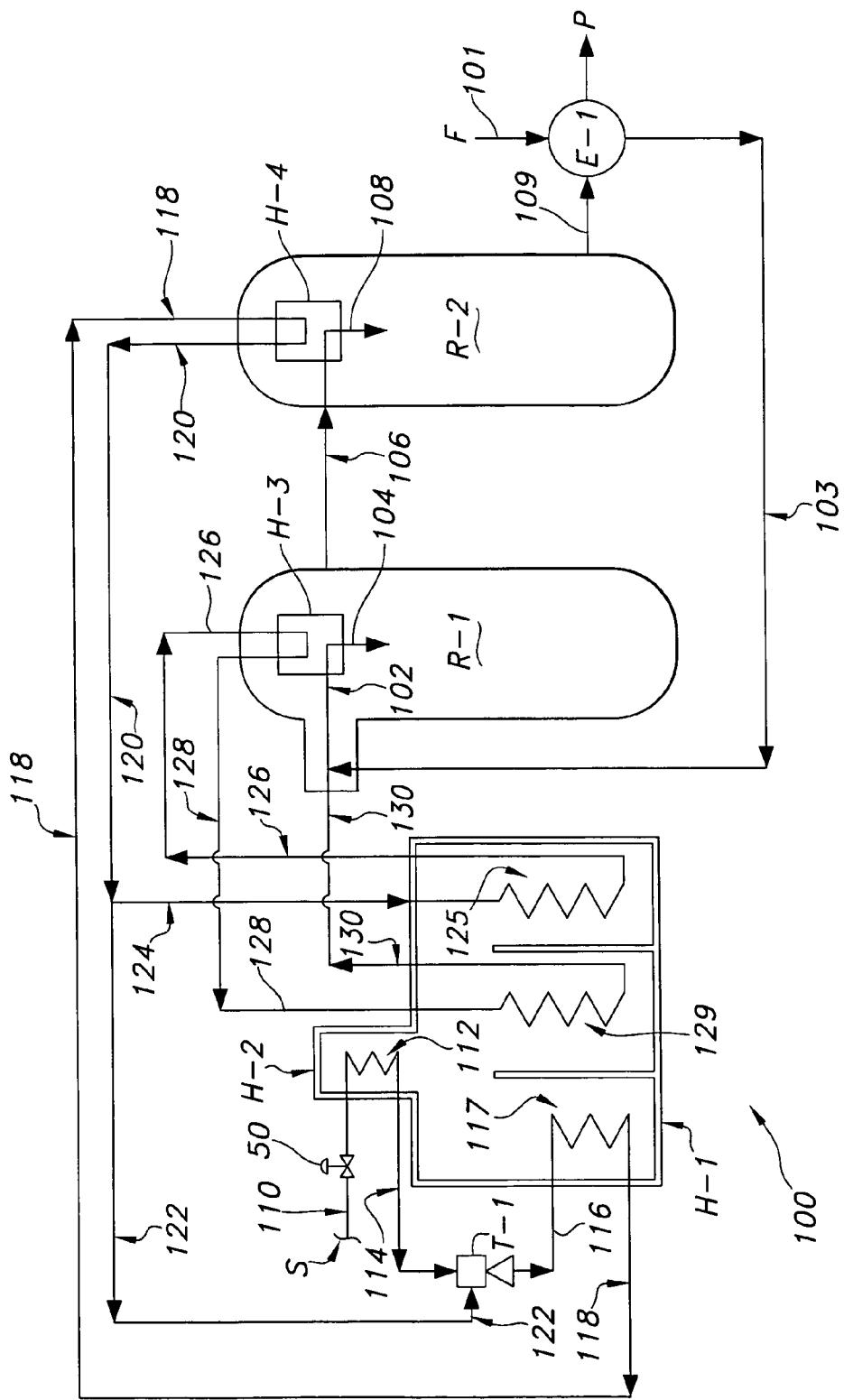
FIG. 2 is a schematic flow diagram of a system and process for the production of styrene from ethylbenzene; and, FIG. 2A is a schematic flow diagram of an alternative embodiment of the system and process for the production of styrene from ethylbenzene.

Referring now to FIG. 2, feed F for the dehydrogenation system 100 includes ethylbenzene and primary steam. The steam to oil ("S/O") ratio of the feed is no more than about 1.0, preferably from about 0.45 to 0.55, more preferably from about 0.49 to about 0.51 for a feed of azeotropic composition.

The advantage to having a feed at the azeotropic composition is that the ethylbenzene-water heterogenous azeotrope boils at about 92° C. at a typical operating pressure of 693 mm Hg absolute, which is less than the boiling point of either water or ethylbenzene at that pressure. Hence, vaporization of the feed is facilitated. Vaporization of the feed can be achieved by heat transfer from the condensing system of the ethylbenzene/styrene monomer splitter ("EB/SM splitter").

Figure 3:
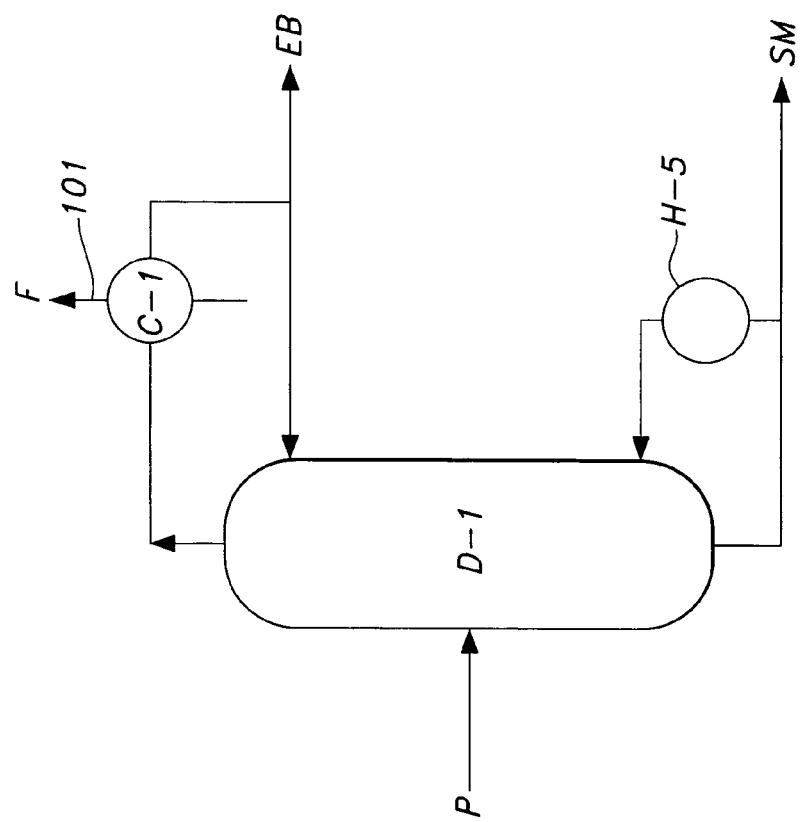
FIG. 3 is a schematic flow diagram of illustrating the vaporization of the feed by using the condenser system of an EB/SM splitter.

Referring now to FIG. 3, the EB/SM splitter D-1 is a conventional distillation column in which the crude styrene product P from the dehydrogenation system 100 is separated into a stream SM, which is rich in styrene monomer, and an overhead of ethylbenzene EB, lighter components, and a low concentration of SM. The overhead is partly condensed in condenser C-1 by using ethylbenzene/water feed mixture as the coolant, thereby transferring heat to, and vaporizing, the feed F. The water component of the feed can be from any suitable source, such as process water. The bottom stream is separated into a recycle stream through reboiler H-5, and a product stream SM rich in styrene monomer. There may be additional condensers to reject some of the heat. For example, the heat can be rejected to cooling water.

Referring again to FIG. 2, the feed F, emerging from the condenser C-1 at approximately 92° C. flows through line 101 to the feed effluent interchanger E-1 where the feed is heated to about 500° C. to about 560° C. and flows through line 103 whereupon it is joined with stream 130 of superheated steam. Stream 130 is at a temperature of from about 800° C. to about 860° C. and is mixed in such proportion with the feed F so as to provide a reactant process stream 102 to reactor R-1 having a temperature of from about 600° C. to about 620° C., when the catalyst is at the start of the run. Reactor R-1 includes a heat exchanger H-3 associated therewith wherein heat is transferred from stream 126 of superheated steam, which is at a temperature of from about 800° C. to about 920° C., to reactant stream 102. Heat exchanger H-3 is preferably a countercurrent heat exchanger, and can be inside the reaction vessel R-1 or exterior to the reaction vessel R-1 (not shown). Sufficient heat is provided to process stream 102 to effect dehydrogenation of the ethylbenzene component. Typically, dehydrogenation of ethylbenzene is performed at an inlet temperature of from about 610° C. to about 650° C., although temperatures outside of this range can also be suitable. Because of the addition of steam to the feed the dehydrogenation reaction can take place in a S/O ratio of ranging from about 0.8 to about 1.7, preferably no more than 1.15, more preferably at 0.90 or less. The reactor R-1 can be a single bed or multibed reactor. Preferably reactor R-1 is a conventional radial flow reactor, although parallel flow reactors or axial flow reactors can alternatively be used. A catalytically effective amount of a conventional catalyst such as one based on iron oxide can be employed in reactor R-1. Suitable catalysts are known to those with skill in the art.

The heated process stream 104 emerges from heat exchanger H-3 preferably at a temperature of from about 610° C. to about 650° C. At least some of the ethylbenzene component of the feed undergoes dehydrogenation in reactor R-1 to produce styrene and hydrogen. The outflow 106 of reactor R-1, which contains some styrene, emerges at a temperature of from about 550° C. to about 580° C. and is introduced into a second reactor R-2, of the same type as reactor R-1. Process stream 106 is passed through heat exchanger H-4 where it is heated by superheated steam stream 118 to a reaction temperature of from about 610° C. to about 650° C. The heated process stream 108 undergoes further reaction. The second reactor R-2 effluent stream 109 is used to preheat the feed F in a feed effluent interchanger E-1. The product P from the feed effluent interchanger E-1 contains crude styrene and some unreacted ethylbenzene with some lighter components (e.g., hydrogen) and is cooled and partly condensed and the liquid is then sent to the EB/SM splitter D-1 (FIG. 3) for further purification.

Main steam S is introduced into the system through line 110 to make up the difference between the amount of steam required to satisfy the overall S/O ratio and the amount of steam vaporized in the condenser C-1 of the EB/SM splitter D-1. Main steam S is initially at a temperature of from about 170° C. to about 190° C. and a pressure of from about 150 to about 160 psia. Valve 50 controls the input of steam. The steam is passed through a heating zone such as convective coil 112 positioned in the convection section H-2 of steam superheater H-1, and the main steam emerges from convective coil 112 into line 114 at a temperature of from about 540° C. to 560° C. and a pressure of from about 130 psia to about 140 psia. The main steam is then sent to a thermocompressor T-1 and is used as compression steam. Thermocompressor T-1 is a steam jet compressor which operates at a compression ratio of from about 1.0 to about 2.5, preferably from about 1.6 to about 1.8, and which boosts a low pressure steam to a higher pressure. Thermocompressors are known and thermocompressors suitable for use in the system of the present invention are commercially available from various suppliers such as, for example, Fox Valve Development Corp. of Dover, N.J. and Artisan Industries Inc., of Waltham, Mass.

The low pressure steam is brought in via line 122 at about 20 to 25 psia and at a temperature of from about 570° C. to about 590° C. The outflow 116 from the thermocompressor T-1 is at a temperature of from about 550° C. to about 570° C. and at a pressure of from about 40 psia to about 50 psia. The steam is then introduced into one of three sections of the steam superheater H-1 through radiant coil 117.

Steam superheater H-1 can be an electric furnace or a furnace burning gas and/or liquid fuels for heating high pressure steam to a superheat temperature sufficient to provide enough heat for the dehydrogenation reaction. An advantage of the system 100 described herein is that the steam superheater H-1 can be operated so as to provide an effluent having a temperature no more than about 927° C., and preferably less than 900° C., more preferably less than 890° C. Operation of the steam superheater at such temperatures avoids the necessity of using costly special alloys for the construction of the superheater H-1 such as would be required for temperatures at above 927° C.

Superheater H-1 is preferably divided into three sections so as to accommodate three tubular coils in the radiant area of the superheater.

The outflow stream 118 from the superheater carries steam at a temperature of from about 850° C. to about 900° C. and a pressure of from about 25 psia to about 35 psia to heat exchanger H-4 in reactor R-2, thereby transferring heat to the reactant stream 106, which is the outflow from reactor R-1. Stream 120, which is the outflow of steam from heat exchanger H-4, is at a temperature of from about 570° C. to about 600° C. and a pressure of from about 24 psia to 28 psia. A first portion of stream 120, i.e., stream 122, is recycled back to the thermocompressor T-1, and a second portion of stream 120, i.e., stream 124, flows back to the steam superheater H-1 radiant coil 125. The portion of the steam flowing through line 124 is heated in radiant coil 125 and emerges via line 126 at a temperature of from about 840° C. to about 860° C. The steam is then carried to heat exchanger H-3 associated with reactor R-1, where it transfers heat to reactant stream 102.

Steam emerges from heat exchanger H-3 at a temperature of from about 620° C. to about 640° C. and is carried via line 128 back to the steam superheater H-1 where it passes through radiant coil 129 and emerges via line 130 as superheated steam at a temperature of from about 840° C. to about 860° C. and a pressure of about 12 psia to about 15 psia. The steam flowing through line 130 is thereupon mixed with the vaporized feed F from line 103 and the combined stream 102 is passed through heat exchanger H-3 and introduced into reactor R-1.

Figure 2A:
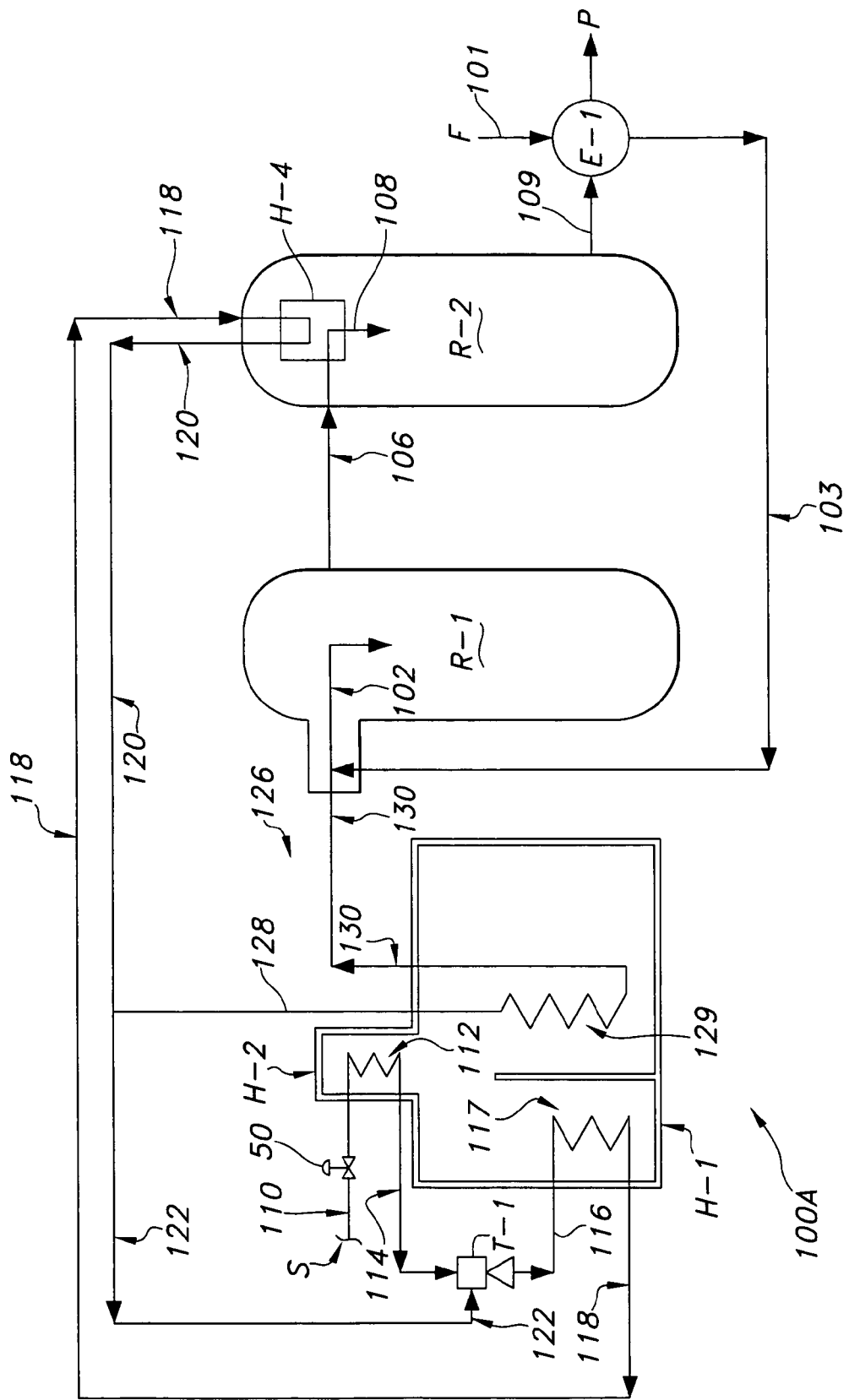

Referring to FIG. 2A, an alternative process 100A is illustrated which is similar to process 100 with the following exceptions: streams 124, 126 and 128 are excluded; there is no heater H-3 associated with reactor R-1; stream 130 is introduced into R-1 directly; stream 128 is split off from stream 120.

More specifically, feed stream F, containing a vaporized azeotropic mixture of ethylbenzene and water is vaporized in EB/SM splitter D-1 in the manner previously described. The vaporized and heated feed stream is sent via line 103 and is combined with superheated steam stream to provide a fluid stream 102. This stream enters a first reaction zone in reactor R-1 where it contacts a dehydrogenation catalyst and undergoes a first stage of conversion to produce at least some styrene. The effluent 106 emerges from reactor R-1 and is heated in countercurrent heat exchanger H-4 and enters a second reaction zone in reactor R-2. The fluid stream is contacted with the dehydrogenation catalyst and undergoes a second stage conversion to produce a stream 108 containing styrene which exits reactor via outlet 109. Effluent stream 109 is used to preheat feedstream F in fees effluent interchanger E-1. The second reactor R-2 effluent stream 109 is used to preheat the feed F in a feed effluent interchanger E-1. The product P from the feed effluent interchanger E-1 contains crude styrene and some unreacted ethylbenzene with some lighter components (e.g., hydrogen) and is cooled and partly condensed and the liquid is then sent to the EB/SM splitter D-1 (FIG. 3) for further purification.

A flow of superheated steam is cycled to the countercurrent heat exchanger H-4 via line 118 to provide heat transferred to the effluent stream 106. The spend steam emerging via line 120 from heat exchanger H-4 is divided into a first portion 122 and a second portion 128. The first portion 122 of spent steam is sent to thermocompressor T-1. A flow 114 main steam S is sent through the thermocompressor to pressurize the first portion 122 via superheater H-1 through convective coil 112. The outflow 116 from thermocompressor T-1 is then heated in steam superheater H-1 to provide the stream 118 which is cycled back to heat exchanger H-4.

The second portion 128 spent steam is sent to steam superheater H-1 where it is reheated via coil 129. Superheated steam 130 emerging from the steam superheater is then combined with the feed stream and sent to reactor R-1.

EXAMPLE 1

Features of the invention are illustrated below in the following prophetic example wherein reference is made to the numerals of the system illustrated in FIG. 2.

A feed stream F of 162,648 kg/hr is provided. The feed stream contains a vaporized azeotropic mixture of ethylbenzene and water having an S/O ratio of 0.493. The vaporized and heated feed stream 103 is at a temperature of 549° C. and at a pressure of 11.1 psia. The feed stream is combined with 44,343 kg/hr of superheated steam (130) at 849° C. and 13 psia to provide a fluid stream 102 of 206,991 kg/hr at an S/O ratio of 0.9. This stream is heated in a countercurrent heat exchanger H-3 and enters a first reaction zone in reactor R-1 at 650° C. and 7.77 psia where it contacts a dehydrogenation catalyst and undergoes a first stage of conversion to produce at least some styrene. The effluent 106 emerges from reactor R-1 at 560° C. and 6.95 psia, and is heated in countercurrent heat exchanger H-4 and enters a second reaction zone in reactor R-2 at 650° C. The fluid stream is contacted with the dehydrogenation catalyst and undergoes a second stage conversion to produce a product stream containing styrene.

A flow in line 118 of 66,511 kg/hr of superheated steam at 889° C. and 31 psia is cycled to the countercurrent heat exchanger H-4 to provide heat transferred to the effluent stream 106. The spent steam emerging from heat exchanger H-4 is divided into a first portion 122 of 22,168 kg/hr and a second portion 124 of 44,343 kg/hr. The first portion 122 of spent steam at 583° C. and 24.5 psia is sent to thermocompressor (T-1). A flow in line 114 of 44,343 kg/hr main steam at 549° C. and 131 psia is sent through the thermocompressor to pressurize the first portion 122. The outflow line 116 of 66,511 kg/hr steam from the thermocompressor is at 559° C. and 40.75 psia, corresponding to a compression ratio of 1.66. The outflow 116 is then heated in steam superheater H-1 to provide the stream 118 which is cycled back to heat exchanger H-4.

The second portion 124 of 44,343 kg/hr spent steam is heated in steam superheater H-1. The outflow 126 from the superheater is sent to heat exchanger H-3 at 850° C. and 22.25 psia to provide heat transferred to the fluid stream 102. Spent steam 128 emerges from the heat exchanger H-3 at 631 degrees C. and 18.74 psia and is sent to steam superheater H-1 where it is reheated to a temperature of 850° C. Superheated steam 130 emerging from the steam superheater is then combined with the feed stream and sent to reactor R-1.

The overall conversion of ethylbenzene across the two reactors is approximately 62.5% with a molar selectivity of about 94.1% styrene.

EXAMPLE 2

Features of the invention are illustrated below in the following prophetic example wherein reference is made to the numerals of the system illustrated in FIG. 2A.

A feed stream F of 193,775 kg/hr is provided. The feed stream contains a vaporized azeotropic mixture of ethylbenzene and water having an S/O ratio of 0.493. The vaporized and heated feed stream 103 is at a temperature of 537° C. and at a pressure of 10.8 psia. The feed stream is combined with 65,803 kg/hr of superheated steam 130 at 890° C. and 10 psia to provide a fluid stream 102 of 259,576 kg/hr at an S/O ratio of 1.0. This stream enters a first reaction zone in reactor R-1 at 620° C. and 8.2 psia where is contacts a dehydrogenation catalyst and undergoes a first stage of conversion to produce at least some styrene. The effluent 106 emerges from reactor R-1 at 534° C. and 7.3 psia, and is heated in countercurrent heat exchanger H-4 and enters a second reaction zone in reactor R-2 at 625° C. The fluid stream is contacted with the dehydrogenation catalyst and undergoes a second stage conversion to produce a product stream containing styrene.

A flow 118 of 84,438 kg/hr of superheated steam at 887° C. and 23 psia is cycled to the countercurrent heat exchanger H-4 to provide heat transferred to the effluent stream 106. The spend steam emerging from heat exchanger H-4 is divided into a first portion 122 of 18,636 hg/hr and a second portion 128 of 65,802 kg/hr. The first portion 122 of spent steam at 581° C. and 17.6 psia is sent to thermocompressor T-1. A flow 114 of 65,802 kg/hr main steam at 700° C. and 133 psia is sent through the thermocompressor to pressurize the first portion 122. The outflow 116 of 84,438 kg/hr steam from the thermocompressor is at 673° C. and 30.7 psia, corresponding to a compression ratio of 1.7. The outflow 116 is then heated in steam superheater H-1 to provide the stream 118 which is cycled back to heat exchanger H-4.

The second portion 128 of 65,802 kg/hr spent steam is sent to steam superheater H-1 where it is reheated to a temperature of 890° C. Superheated steam 130 emerging from the steam superheater is then combined with the feed stream and sent to reactor R-1.

The overall conversion of ethylbenzene across the two reactors is approximately 62.5% with a molar selectivity of about 94.3% styrene.

EXAMPLE 3

Features of the invention are illustrated below in the following prophetic example wherein reference is made to the numerals of the system illustrated in FIG. 2.

A feed stream F of 159,226 kg/hr is provided. The feed stream contains a vaporized azeotropic mixture of ethylbenzene and water having an S/O ratio of 0.493. The vaporized and heated feed stream 103 is at a temperature of 531° C. and at a pressure of 10.6 psia. The feed stream is combined with 70,087 kg/hr of superheated steam 130 at 852° C. and 10.2 psia to provide a fluid stream 104 of 229,312 kg/hr at an S/O ratio of 1.15. This stream enters a first reaction zone in reactor R-1 at 621° C. and 8.0 psia where is contacts a dehydrogenation catalyst and undergoes a first stage of conversion to produce at least some styrene. The effluent 106 emerges from reactor R-1 at 540° C. and 7.1 psia, and is heated in countercurrent heat exchanger H-4 and enters a second reaction zone in reactor R-2 at 626° C. The fluid stream is contacted with the dehydrogenation catalyst and undergoes a second stage conversion to produce a product stream containing styrene.

A flow 118 of 106,646 kg/hr of superheated steam at 794° C. and 21 psia is cycled to the countercurrent heat exchanger H-4 to provide heat transferred to the effluent stream 106. The spent steam emerging from heat exchanger H-4 is divided into a first portion 122 of 36,560 kg/hr and a second portion 128 of 70,087 kg/hr. The first portion 122 of spent steam at 587° C. and 17.8 psia is sent to thermocompressor T-1. A flow 114 of 70,086 kg/hr main steam at 700° C. and 133 psia is sent through the thermocompressor to pressurize the first portion 122. The outflow 116 of 106,646 kg/hr steam from the thermocompressor is at 661° C. and 30.7 psia, corresponding to a compression ratio of 1.7. The outflow 116 is then heated in steam superheater H-1 to provide the stream 118 which is cycled back to heat exchanger H-4.

The second portion 128 of 70,087 kg/hr spent steam is sent to steam superheater H-1 where it is reheated to a temperature of 852° C. Superheated steam 130 emerging from the steam superheater is then combined with the feed stream F and sent to reactor R-1.

The overall conversion of ethylbenzene across the two reactors is approximately 62.6% with a molar selectivity of about 94.9% styrene.

Example 3 has a higher steam consumption that Example 2. However, for example 3, stream 118 is below 815° even when the catalyst is at end of run. Therefore, the material of construction of this line can be 304 H stainless steel instead of some more expensive material such as Alloy 800 H. In example 3, the current total cost of piping using Alloy 800 H is approximately $900,000. In contrast, the current total cost of using 304 H stainless steel is $230,000. By utilizing the novel flow scheme in Example 3, a net savings in piping material alone is $670,000.

While the above description contains many specifics, these specifics should not be construed as limitations on the scope of the invention, but merely as exemplifications of preferred embodiments thereof. Those skilled in the art will envision many other possibilities within the scope and spirit of the invention as defined by the claims appended hereto.

What is claimed is:

1. A method for providing heat to a chemical conversion process stream containing at least one chemical reactant, comprising the steps of:
   a) superheating a heat transfer fluid;
   b) transferring heat from the superheated heat transfer fluid to a process stream;
   c) dividing at least some of the heat transfer fluid after transferring heat in step b into a first portion and a second portion;
   d) pressurizing the first portion of heat transfer fluid;
   e) recycling the pressurized first portion of heat transfer fluid to superheating step (a); and,
   f) introducing the second portion of the heat transfer fluid into the process stream.

2. The method of claim 1 further comprising the step of drawing off at least a third portion of the heat transfer fluid after the transferring heat step (b) and before the dividing step (c).

3. The method of claim 1 wherein the recycling step is performed a plurality of times.

4. The method of claim 1 further comprising a step of superheating the second portion of heat transfer fluid before step (f).

5. The method of claim 2 further comprising a step of superheating the second portion of heat transfer fluid before step (f).

6. The method of claim 1 wherein the step (d) of pressurizing the first portion of heat transfer fluid comprises introducing the first portion of heat transfer fluid into a thermocompressor and introducing a compression fluid into the thermocompressor, the compression fluid being at a higher pressure than the first portion of heat transfer fluid.

7. The method of claim 6 wherein the heat transfer fluid and compression fluid are steam.

8. The method of claim 1 wherein the heat transfer fluid is steam.

9. The method of claim 8 wherein the chemical conversion process comprises dehydrogenation and the chemical reactant is a compound selected from the group consisting of ethylbenzene, ethyl toluene, propane and butane.

10. The method of claim 9 wherein the chemical conversion process comprises the production of styrene by the dehydrogenation of ethylbenzene.

* * * * *